US010440996B2

(12) United States Patent
Manca et al.

(10) Patent No.: US 10,440,996 B2
(45) Date of Patent: Oct. 15, 2019

(54) ATOMIZING ASSEMBLY FOR USE IN AN AEROSOL-GENERATING SYSTEM

(71) Applicant: Altria Client Services LLC, Richmond, VA (US)

(72) Inventors: Laurent Manca, Sullens (CH); Rui Nuno Batista, Morges (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/474,317

(22) Filed: Mar. 30, 2017

(65) Prior Publication Data

US 2017/0280775 A1    Oct. 5, 2017

Related U.S. Application Data

(63) Continuation of application No. PCT/EP2017/054243, filed on Feb. 23, 2017.

(30) Foreign Application Priority Data

Mar. 31, 2016    (EP) .................................... 16163421

(51) Int. Cl.
  *A24F 47/00*  (2006.01)
  *B05B 7/16*   (2006.01)
  *B05B 7/24*   (2006.01)
(52) U.S. Cl.
  CPC .......... *A24F 47/008* (2013.01); *B05B 7/1686* (2013.01); *B05B 7/2464* (2013.01)

(58) Field of Classification Search
  CPC .... A24F 47/008; A24F 47/002; A24F 47/004; A24F 13/02; A24F 47/00; A24F 7/04;
  (Continued)

(56) References Cited

U.S. PATENT DOCUMENTS 5,285,798 A    2/1994  Banerjee et al.
5,666,977 A    9/1997  Higgins et al.
  (Continued)

FOREIGN PATENT DOCUMENTS

EP    0845220 A1   6/1998
EP    0957959 B1   9/2007
  (Continued)

OTHER PUBLICATIONS

Extended European search report 16163421.7-1662 dated Jun. 7, 2016.
  (Continued)

*Primary Examiner* — Truc T Nguyen
(74) *Attorney, Agent, or Firm* — Harness, Dickey & Pierce, P.L.C.

(57) ABSTRACT

An atomizing assembly includes a tubing section having an inlet end and an outlet end. The inlet end of the tubing section is connectable to a liquid storage portion, and the outlet end of the tubing section is in fluid communication with an atomizing nozzle. The tubing section is configured to deliver a flow of liquid aerosol-forming substrate through the atomizing nozzle. The atomizing nozzle includes an air channel configured to establish an air flow through the nozzle. The air flow is mixed with the flow of liquid aerosol-forming substrate.

13 Claims, 2 Drawing Sheets

(58) Field of Classification Search
CPC ...... H05B 3/42; H05B 1/0244; H05B 1/0291; H05B 1/0297; H05B 3/03; H05B 3/06; H05B 3/0014; H05B 2203/021; H05B 3/026
See application file for complete search history.

(56) References Cited

U.S. PATENT DOCUMENTS

| | | | |
|---|---|---|---|
| 6,103,810 A | 8/2000 | Frayer et al. | |
| 6,158,676 A * | 12/2000 | Hughes | A61M 11/06 239/337 |
| 6,196,218 B1 * | 3/2001 | Voges | A24F 47/002 128/200.14 |
| 7,337,768 B2 * | 3/2008 | Elia | F02M 43/04 123/549 |
| 7,357,124 B2 * | 4/2008 | Elia | F02M 51/0639 123/179.21 |
| 2006/0196518 A1 * | 9/2006 | Hon | A24F 47/002 131/360 |
| 2008/0230052 A1 | 9/2008 | Montaser | |
| 2009/0272379 A1 * | 11/2009 | Thorens | A24F 47/008 128/202.21 |
| 2011/0094523 A1 * | 4/2011 | Thorens | A24F 47/008 131/194 |
| 2013/0228191 A1 * | 9/2013 | Newton | A24F 47/008 131/329 |
| 2013/0319407 A1 * | 12/2013 | Liu | A61M 15/06 128/202.21 |
| 2014/0060554 A1 | 3/2014 | Collett et al. | |
| 2014/0109905 A1 * | 4/2014 | Yamada | A61M 15/06 128/203.27 |
| 2014/0261486 A1 | 9/2014 | Potter et al. | |
| 2015/0117842 A1 * | 4/2015 | Brammer | H05B 3/02 392/387 |
| 2015/0136158 A1 * | 5/2015 | Stevens | A24F 47/008 131/329 |
| 2015/0216236 A1 * | 8/2015 | Bless | A24F 47/008 131/328 |
| 2015/0276262 A1 | 10/2015 | Dai et al. | |
| 2015/0335071 A1 * | 11/2015 | Brinkley | F22B 1/284 131/328 |
| 2016/0073692 A1 * | 3/2016 | Alarcon | A24F 47/008 131/329 |
| 2016/0100633 A1 * | 4/2016 | Gao | A24F 47/008 131/329 |
| 2016/0213065 A1 * | 7/2016 | Wensley | A24F 47/008 |
| 2016/0332754 A1 * | 11/2016 | Brown | B65B 3/10 |
| 2017/0251727 A1 | 9/2017 | Nielsen | |
| 2017/0280776 A1 | 10/2017 | Manca et al. | |
| 2017/0280777 A1 | 10/2017 | Manca et al. | |
| 2017/0303590 A1 | 10/2017 | Cameron et al. | |
| 2018/0213845 A1 * | 8/2018 | Qiu | H05B 3/03 |
| 2018/0255834 A1 * | 9/2018 | Dillmann | A24F 47/004 |
| 2018/0343922 A1 * | 12/2018 | Stadler | A24F 47/004 |

FOREIGN PATENT DOCUMENTS

| | | |
|---|---|---|
| WO | WO-2005065756 A2 | 7/2005 |
| WO | WO-2009103063 A2 | 8/2009 |
| WO | WO-2012062600 A1 | 5/2012 |
| WO | WO-2013083635 A1 | 6/2013 |
| WO | WO-2016/005530 A1 | 1/2016 |
| WO | WO-2016/005531 A1 | 1/2016 |
| WO | WO-2016/005533 A1 | 1/2016 |
| WO | WO-2016/005600 A1 | 1/2016 |
| WO | WO-2016/005601 A1 | 1/2016 |
| WO | WO-2016/005602 A1 | 1/2016 |

OTHER PUBLICATIONS

International Search Report and Written Opinion dated May 12, 2017 in International Application No. PCt/EP2017/054243.
United States Office Action for corresponding U.S. Appl. No. 16/009,703 dated Nov. 13, 2018.
International Preliminary Report on Patentability and Written Opinion for International Application No. PCT/EP2017/054243 dated Oct. 2, 2018.
Innovation in Miniature, Lee Products Ltd, Check Valves, pp. 1-3, Mar. 18, 2019, http://www.industrial-microhydraulics.co.uk/check_valves.htm.
Morphy Richards, Redefine, It's time to redefine your expectations, 1-2 Mar. 18, 2019, http://www.morphyrichardsredefine.com.
Innovation in Miniature, Lee Products Ltd, Precision Fluid Control Components, pp. 1-2, Mar. 18, 2019, http://www.leeproducts.co.uk.
Spraying Systems Co., Experts in Spray Technology, pp. 1-6, Mar. 18, 2019, https://www.spray.com.
U.S. Notice Of Allowance for corresponding U.S. Appl. No. 16/009,703 dated Mar. 27, 2019.
United States Office Action for corresponding U.S. Appl. No. 16/009,703 dated Jul. 9, 2019.

* cited by examiner

ATOMIZING ASSEMBLY FOR USE IN AN AEROSOL-GENERATING SYSTEM

This is a continuation of and claims priority to PCT/EP2017/054243 filed on Feb. 23, 2017, and further claims priority to EP 16163421.7 filed on Mar. 31, 2016; both of which are hereby incorporated by reference in their entirety.

BACKGROUND

One type of an aerosol generating system is an electrically operated aerosol generating system. Handheld electrically operated aerosol generating systems consist of a device portion comprising a battery and control electronics, a cartridge portion comprising a supply of aerosol-forming substrate held in a liquid storage portion, and an electrically operated vaporizer, and a mouthpiece. The vaporizer comprises a coil of heater wire wound around an elongate wick soaked in the liquid aerosol forming substrate held in the liquid storage portion.

EP 0 957 959 B1 discloses an electrically operated aerosol generator configured to receive liquid material from a source. The aerosol generator comprises a pump for pumping the liquid material in metered amounts from the source through a tube with an open end. A heating element surrounds the tube. The liquid material within the tube is volatilized upon activation of the heater. Upon volatilization the liquid material expands and exits the open end of the tube in gaseous form.

Residues may be created upon heating. In capillary tubes, the residues can cause clogging. This effect can alter liquid transport properties. Furthermore, the liquid material is heated indirectly: first the tube or a capillary wick is heated which in turn heats the liquid material. Heat can be lost during the energy transfer process.

Moreover, volatilization in the above described system is rather slow, as a substantial amount of liquid is to be volatilized in the confined volume within the tube.

It would be desirable to provide an improved aerosol generating system with a low-maintenance liquid transport system and with an improved atomization effect.

SUMMARY

At least one example embodiment relates to an atomizing assembly for an aerosol-generating system.

In at least one example embodiment, an atomizing assembly for an aerosol-generating system comprises an atomizing nozzle defining an air channel, the air channel configured to establish an air flow through the nozzle; a liquid storage portion configured to store a liquid aerosol forming substrate; and a tubing section having an inlet end and an outlet end. The inlet end of the tubing section is connectable to the liquid storage portion. The outlet end of the tubing section is in fluid communication with the atomizing nozzle. The tubing section is configured to deliver a flow of the liquid aerosol forming substrate through the atomizing nozzle. The air flow is mixed with the flow of liquid aerosol forming substrate delivered through the atomizing nozzle.

At least one example embodiment relates to an aerosol generating system.

In at least one example embodiment, an aerosol-generating system comprises a housing; an air inlet in the housing; a mouthpiece at an end of the housing, an air flow path extending from the air inlet to the mouthpiece; and an atomizing assembly. The atomizing assembly includes an atomizing nozzle defining an air channel, the air channel configured to establish an air flow through the nozzle; a liquid storage portion configured to store a liquid aerosol forming substrate; and a tubing section having an inlet end and an outlet end. The inlet end of the tubing section is connectable to the liquid storage portion. The outlet end of the tubing section is in fluid communication with the atomizing nozzle. The tubing section is configured to deliver a flow of the liquid aerosol forming substrate through the atomizing nozzle. The air flow is mixed with the flow of liquid aerosol forming substrate delivered through the atomizing nozzle.

BRIEF DESCRIPTION OF THE DRAWINGS

Example embodiments will now be described with reference to the accompanying drawings.

DETAILED DESCRIPTION

Figure 1:
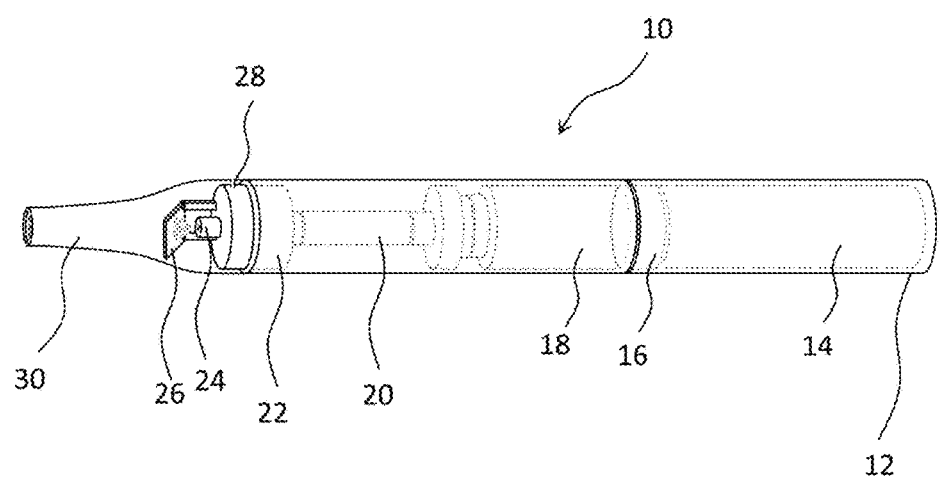
FIG. 1 is a side view of an aerosol generating system including an atomizer according to at least one example embodiment.

Various example embodiments will now be described more fully with reference to the accompanying drawings in which some example embodiments are shown. However, specific structural and functional details disclosed herein are merely representative for purposes of describing example embodiments. Thus, the embodiments may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including,"

if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative ter. ms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

In order to more specifically describe example embodiments, various features will be described in detail with reference to the attached drawings. However, example embodiments described are not limited thereto.

At least one example embodiment relates to an atomizing assembly of an aerosol generating system, such as a handheld electrically operated aerosol generating system. At least one example embodiment relates to an aerosol generating system comprising an atomizing assembly. At least one example embodiment relates to a method of generating an aerosol in an aerosol generating system.

An atomizing assembly for an aerosol generating system, comprises a tubing section for conveying a liquid aerosol-forming substrate. The tubing section includes an inlet end and an outlet end. The inlet end of the tubing section is configured to be connected to a liquid storage portion, and the outlet end of the tubing section is connected to an atomizing nozzle. The tubing section is configured to deliver a flow of liquid aerosol forming substrate through the atomizing nozzle. The atomizing nozzle comprises an air channel configured to establish an air flow through the atomizing nozzle. The air flow is mixed with the flow of liquid aerosol forming substrate to enhance atomization of the flow of liquid aerosol forming substrate delivered through the atomizing nozzle.

In at least one example embodiment, the liquid aerosol forming substrate is finely distributed into a spray jet of small droplets. By mixing the spray jet with the air stream atomization of the liquid aerosol forming substrate can be enhanced. The average size of the droplets may be reduced. The liquid may be more homogeneously distributed and may be fully, i.e. without residues, and quickly volatilized by a downstream heater element. In this way a reproducible aerosol generation can be achieved.

The tubing section may comprise a pumping unit configured to controllably deliver a desired (or, alternatively predetermined) amount of liquid aerosol forming substrate through the atomizing nozzle. The pumping unit may be any commercially available pumping system, such as an electrically driven pump, a motorized pump, a micro pump, or a manually operated pump. The pumping unit is configured to transport the liquid aerosol forming substrate from the liquid storage portion to the atomizing nozzle. The pumping unit is further configured to deliver the liquid aerosol forming substrate with a slight over pressure to the atomizing nozzle such that the liquid aerosol forming substrate is transformed into a spray jet.

In at least one example embodiment, alternatively to using a pumping unit for conveying the liquid aerosol forming substrate from the liquid storage portion to the atomizing nozzle, it is also possible use a liquid storage portion comprising pressurized liquid aerosol forming substrate. The tubing section may then comprise a controllable one-way valve which may be configured to deliver a metered amount of liquid aerosol forming substrate to the atomizing nozzle upon activation. The liquid aerosol forming substrate may be pressurized in the liquid storage portion by mechanical means or by adding suitable propellants to the liquid aerosol forming substrate. Mechanical means may include elastic collapsible containers or pumping systems.

The inlet portion of the tubing section is configured for connection to a liquid storage portion. The connection between the tubing section and the liquid storage portion may be a permanent connection or a releasable connection. In at least one example embodiment, the liquid storage portion may be refillable. In at least one example embodiment, the liquid storage portion may be replaceable and may be exchanged when it is empty or when a different type of liquid substrate for aerosol generation is desired. The releasable connection between the tubing section and the liquid storage portion may be established by any suitable connection means, including a Luer taper connection (either the locking or fitting type).

The tubing section may further comprise at least one one-way valve configured to control fluid flow through the tubing section. Any commercially available one-way valves with adequate size and liquid flows may be included, including mini and micro flutter valves, duckbill valves, check valves. The valves may be made of any suitable material for example materials, which may be used for food industry or medical applications.

The liquid aerosol-forming substrates are characterized by a relatively high viscosity as compared to water. The viscosity of a liquid aerosol-forming substrate may be in the range from about 10 millipascal seconds to about 500 millipascal seconds, or in the range from about 17 millipascal seconds to about 86 millipascal seconds. The liquid aerosol forming substrate is a substrate that may release volatile compounds that can form an aerosol. The volatile compounds may be released by heating the liquid aerosol forming substrate. The liquid aerosol forming substrate may comprise plant-based material. The liquid aerosol forming substrate may comprise tobacco. The liquid aerosol forming substrate may comprise a tobacco-containing material containing volatile tobacco flavor compounds, which are released from the liquid aerosol forming substrate upon heating. The liquid aerosol forming substrate may alternatively comprise a non-tobacco-containing material. The liquid aerosol forming substrate may comprise homogenized plant-based material. The liquid aerosol forming substrate may comprise homogenized tobacco material. The liquid aerosol forming substrate may comprise at least one aerosol former. The liquid aerosol forming substrate may comprise other additives and ingredients, such as flavorants.

In at least one example embodiment, an aerosol generating system, comprises the above disclosed atomizing assembly and further comprises a housing with an air inlet and a mouthpiece so as to establish an air flow path from the air inlet to the mouthpiece.

When the mouthpiece is drawn upon, an air flow is generated in the air flow path between the air inlet and the mouthpiece so that at least a portion of this air flow is guided through the air channel of the atomizing nozzle. The air flow is mixed with the flow of liquid aerosol-forming substrate thereby enhancing an atomization effect of the spray nozzle.

The air flow through the atomizing nozzle may be mixed with the flow of liquid aerosol-forming substrate within the atomizing nozzle and the mixed flow may be delivered through a common outlet end of the atomizing nozzle.

In at least one example embodiment, the air flow through the atomizing nozzle and the flow of liquid aerosol forming substrate are delivered through separate outlets provided in the atomizing nozzle. In at least one example embodiment, the atomizing nozzle may have a central outlet opening for the liquid aerosol forming substrate, which creates a spray jet of small droplets of liquid aerosol forming substrate. A ringshaped outlet opening arranged radially outwardly from and concentrically with the central opening may be provided as air stream outlet opening. The air stream mixes with the spray jet downstream from the outlet openings.

The atomizing nozzle may comprise a plurality of outlet openings for each of the air flow and the flow of liquid aerosol forming substrate.

Commercially available atomizing nozzles may use specific caps that induce an airflow management in the outlet of the nozzle that create a defined geometry of the spray jet. The cap of the atomizing nozzle may be designed or selected from existing models in the market, to create a geometry and size of the spray to match the geometry and size of the hot surface of the heating element.

The aerosol generating system may be configured to define further secondary air flow paths in addition to the primary air flow path through the atomizing nozzle. The additional air flows may recombine before or after aerosol generation in order to achieve a desired air flow composition.

If secondary air inlets are provided, only a portion of the total air stream generated is guided through the air channel of the atomizing nozzle. In at least one example embodiment, about 30 percent to about 90 percent, or about 50 percent to about 70 percent of the total air flow is guided through the air channel of the atomizing nozzle.

The spray jet generated by the atomization nozzle may be directed on a heater assembly. The heater assembly may comprise any type of heating elements suitable for evaporating the liquid aerosol forming substrate. The heater assembly may be substantially flat and may have any desired shape. The heater assembly may have a rectangular, polygonal, circular or oval shape with width and length dimensions ranging from about 3 millimeters to about 10 millimeters.

The heating element may comprise a thin, substantially flat, electrically conductive material, such as a mesh of fibers, a conductive film, or an array of heating strips, suitable for receiving and heating an aerosol forming substrate in an aerosol generating system.

The heating element may comprise a plurality of openings. In at least one example embodiment, the heating element may comprise a mesh of fibers with interstices therebetween. The heating element may comprise a thin film or plate, optionally perforated with small holes. The heating element may comprise an array of narrow heating strips connected in series.

The heater assembly may comprise a heat resistive substrate and a heating element provided in the heat resistive substrate or on a surface of the heat resistive substrate. The heat resistive substrate of the heater assembly may be made from glass, heat resistive glass, ceramics, silicon, semiconductors, metals or metal alloys.

The heat resistive substrate may be substantially flat and may have any desired shape. The heat resistive substrate may have a rectangular, polygonal, circular, or oval shape with width and length dimensions ranging from about 3 millimeters to about 10 millimeters. The thickness of the heat resistive substrate may range from about 0.2 millimeter to about 2.5 millimeters. In at least one example embodiment, the heat resistive substrate may be have a rectangular shape with a size of about 7×6 millimeters or 5×5 millimeters×W).

The heating element may be provided as a thin film coating provided to the surface of the heat resistive substrate. The heating element can be impregnated, deposited, or printed on the surface of the heat resistive substrate. The material of the thin film heating element can be any suitable material which has convenient electrical properties and a sufficiently high adherence to the heat resistive substrate.

The heating element may be provided within the volume of the heat resistive substrate, may be sandwiched between two elements of the heat resistive substrate, or may be covered with a protective layer of heat resistive material.

In at least one example embodiment, the liquid aerosol forming substrate may be delivered to a front side of the heat resistive substrate and the heating element may be provided on a backside of the heat resistive substrate.

The heater assembly may be spaced apart from the dispensing assembly. By providing the heater assembly spaced apart from the delivery assembly, the amount of liquid aerosol forming substrate delivered to the heater assembly can be better controlled compared to a vaporizer having a tubing segment for carrying flow of the liquid aerosol forming substrate from the delivery assembly to the heater assembly. Undesired capillary actions due to such tubing segment may be avoided. When passing the air gap, the delivered amount of the liquid aerosol forming substrate will be transformed into a jet of droplets before hitting the surface of the heater assembly. Thus, a substantially uniform distribution of the delivered amount of the liquid aerosol forming substrate on the heater assembly can be enhanced in some example embodiments, leading to better controllability and repeatability of generating an aerosol with a desired (or, alternatively predetermined) amount of vaporized aerosol forming substrate per inhalation cycle.

The operating temperature of the heater assembly may range from about 120 degrees Celsius to about 210 degrees Celsius, or from about 150 degrees Celsius to about 180 degrees Celsius. The operation temperature of the device may be varied in some example embodiments.

The flow rate of the liquid aerosol-forming substrate delivered through the atomizing nozzle is within about 0.5 microliters per second to about 2 microliters per second. In at least one example embodiment, comprising a micropump, the micropump may allow on-demand delivery of liquid aerosol-forming substrate at a flow rate of about 0,7 microliters per second to about 4.0 microliters per second for intervals of variable or constant duration. A pumped volume of one activation cycle may be about 0.5 microliters in micropumps working within a pumping frequency ranging from about 8 hertz to about 15 hertz. In at least one example embodiment, the pump volume in each activation cycle, as a dose of liquid aerosol forming substrate per puff, may range form about 0.4 microliters to about 0.5 microliters.

The aerosol generating system may comprise an operation detection unit configured to detect an operation to initiate aerosol generation. The operation detection unit may include a puff detection system, e.g. a puff sensor. In at least one example embodiment, the operation detection unit may include an on-off button, e.g. an electrical switch.

The aerosol generating system further comprises a control unit configured to control delivery of the liquid aerosol forming substrate and to activate the heater assembly. Delivery of the liquid aerosol forming substrate may be time delayed after activation of the heater assembly in response to a detected operation. Upon activation, such as using an on-off button or the puff sensor, the control unit may activate the heater assembly first, and then, after delay of about 0.3 second to about 1 second, or from about 0.5 second to about 0.8 second, may activate the delivery device. The duration of activation may be fixed or may correspond to an action like pressing the on-off button or puffing as e.g. detected by the operation detection unit. In at least one example embodiment, the control unit may be configured to activate the heater assembly and the liquid delivery simultaneously, depending on how fast the heater will react to achieve the desired temperature to produce the aerosol. In at least one example embodiment, the heater may be activated at the start of vaping and kept powered during vaping of the device for any given time span.

In at least one example embodiment, the aerosol generating may comprise a device portion and a replaceable liquid storage portion. The device portion may comprise a power supply and the control unit. The power supply may be any type of electric power supply, typically a battery. The power supply for the delivery device may be different from the power supply of the mesh heating element or may be the same.

The power supply may be a form of charge storage device such as a capacitor, a super-capacitor, or hyper-capacitor. The power supply may require recharging and may have a capacity that allows for the storage of enough energy; for example, the power supply may have sufficient capacity to allow for the continuous generation of aerosol for a period of about six minutes or for a period that is a multiple of about six minutes. In at least one example embodiment, the power supply may have sufficient capacity to allow for a desired (or, alternatively predetermined) number of puffs or discrete activations of the vaporizer.

The aerosol generating system may be an electrically operated system at least one example embodiment, the aerosol generating system is portable. The aerosol generating system may have a size comparable to a cigar or a cigarette. The aerosol generating system may have a total length ranging from about 45 millimeters to about 160 millimeters. The aerosol generating system may have an external diameter ranging from about 7 millimeters to about 25 millimeters.

In at least one example embodiment, a method for generating an aerosol comprises providing an aerosol generating device including a tubing section having an inlet end and an outlet end. The inlet end of the tubing section is configured to be connected to a liquid storage portion. The aerosol generating device also includes an atomizing nozzle at the outlet end of the tubing section, and delivering a flow of liquid aerosol forming substrate through the atomizing nozzle. The atomizing nozzle comprises an air channel configured to establish an air flow through the nozzle. The method further comprises mixing the air flow with the flow of liquid aerosol forming substrate to enhance atomization of the flow of liquid aerosol forming substrate delivered through the atomizing nozzle.

The air flow through the atomizing nozzle is generated when a puff is drawn at the mouthpiece of the aerosol generating system. At least a portion of the air flow between the air inlet and the mouthpiece is guided through the air channel of the atomizing nozzle.

By simultaneously utilizing a drawing action for generation of an air stream through the atomizing nozzle, atomization of the liquid aerosol forming substrate is substantially enhanced, requiring at the same time only very limited modification to existing aerosol generating systems.

Features described in relation to one aspect may equally be applied to other aspects of the invention.

FIG. 1 is an illustration of an aerosol generating system shown with a transparent housing so that internal portions of the aerosol generating system are shown. The aerosol generating system 10 comprises a housing 12, a power source 14, a control unit 16, a liquid storage portion 18, a tubing section 20, a micro pump 22, an atomizing nozzle 24, and a heater assembly 26. The housing comprises an air inlet 28 and a mouthpiece 30 at its proximal end.

The aerosol generating system 10 may be activated by manual operation of a power switch, or may automatically by corresponding detection means when a puff is drawn. Upon detection of a puff, the control unit 16 activates the micropump 22 and the heater assembly 26. The micropump 22 delivers a desired (or, alternatively predetermined) amount of the liquid aerosol forming substrate via atomizing nozzle 24 onto the heater assembly 26 where the liquid aerosol forming substrate is vaporized and is delivered in the form of an aerosol via the mouthpiece 30.

Figure 2:
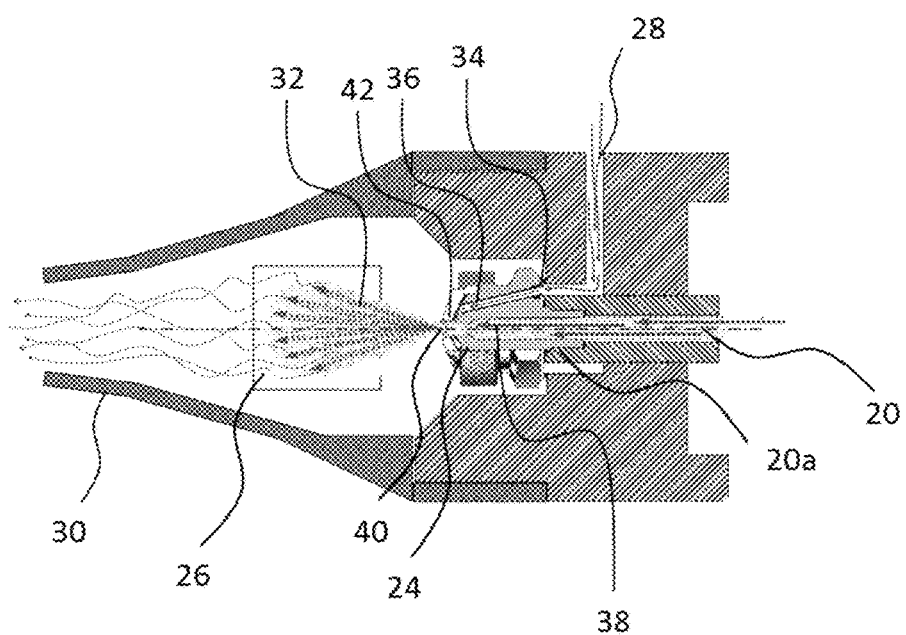
FIG. 2 is an enlarged, cross-sectional view of the the aerosol generating system of FIG. 1 comprising the atomizer according to at least one example embodiment.

FIG. 2 is an enlarged view of the aerosol generating system of FIG. 1, depicting the air flow channel 36 and the fluid flow path 38 through the atomizing assembly in more detail. In at least one example embodiment, as shown in FIG. 2, the atomizing nozzle 24 transforms the liquid aerosol forming substrate into a spray jet 32 of small droplets. This atomization effect is supported by an air stream 34 established in an air flow channel 36 of the atomizing nozzle 24. The liquid aerosol-forming substrate is conveyed in tubing 20 (shown in FIG. 1) towards atomizing nozzle 24 provided at the outlet end 20a of the tubing section 20. The atomizing nozzle 24 has a central outlet 40 opening configured to create a spray jet of small droplets of liquid aerosol forming substrate. The atomizing nozzle 24 further comprises an air flow channel 36 that is in fluid communication with air inlet 28 and which terminates in a ring-shaped outlet opening 42 arranged radially outwardly from and symmetrically with the central opening 40. The air stream 34 exiting the ringshaped outlet opening 42 mixes with the spray jet and enhances atomization of the small droplets of liquid aerosol-forming substrate.

The spray jet 32 is delivered onto heater assembly 26 where the aerosol forming substrate is volatilized to form an aerosol. In at least one example embodiment, the complete air flow is guided through the air flow channel 36 of the atomizing nozzle 24. In at least one example embodiment, additional secondary air inlets may be provided in the housing of the aerosol generating system. The side air flow entering the secondary air inlets may be mixed with the primary flow before or after volatilization by the heater assembly.

The example embodiment described above illustrates but is not limiting. In view of the above discussed example embodiment, other example embodiments consistent with the above example embodiment will now be apparent to one of ordinary skill in the art.

We claim:

1. An atomizing assembly for an aerosol generating system comprising:
   an atomizing nozzle defining an air channel and a fluid flow path, the air channel configured to establish an air flow through the atomizing nozzle and the fluid flow path configured to establish a fluid flow through the atomizing nozzle;
   a liquid storage portion configured to store a liquid aerosol-forming substrate; and
   a tubing section having an inlet end and an outlet end, the inlet end of the tubing section being connectable to the liquid storage portion, and the outlet end of the tubing section being in fluid communication with the atomizing nozzle, the tubing section being configured to deliver the fluid flow of the liquid aerosol-forming substrate through the atomizing nozzle via the fluid flow path, the air flow being mixed with the fluid flow of liquid aerosol-forming substrate delivered through the atomizing nozzle;
   wherein the tubing section comprises a pump configured to controllably deliver an amount of the liquid aerosol forming substrate through the atomizing nozzle.

2. The atomizing assembly according to claim 1, wherein the pump is one of an electrically driven pump, a motorized pump, or a manually operated pump.

3. The atomizing assembly according to claim 1, wherein the liquid storage portion is pressurized.

4. The atomizing assembly according to claim 1, wherein the tubing section comprises,
   at least one one-way valve configured to control liquid flow through the tubing section.

5. An aerosol-generating system comprising:
   a housing;
   an air inlet in the housing;
   a mouthpiece at an end of the housing, an air flow path extending from the air inlet to the mouthpiece;

a heater element; and an atomizing assembly including, an atomizing nozzle defining an air channel, the air channel configured to establish an air flow through the atomizing nozzle, the atomizing nozzle spaced apart from the heater element, and the atomizing nozzle configured to spray a liquid aerosol-forming substrate onto the heater element;

a liquid storage portion configured to store the liquid aerosol-forming substrate; and a tubing section having an inlet end and an outlet end, the inlet end of the tubing section being connectable to the liquid storage portion, and the outlet end of the tubing section being in fluid communication with the atomizing nozzle, the tubing section being configured to deliver a flow of the liquid aerosol-forming substrate through the atomizing nozzle, the air flow being mixed with the flow of liquid aerosol-forming substrate delivered through the atomizing nozzle.

6. The aerosol-generating system according to claim 5, wherein the air flow through the atomizing nozzle is generated in response to a draw at the mouthpiece of the aerosol generating system, wherein at least a portion of the air flow between the air inlet and the mouthpiece is guided through the air channel of the atomizing nozzle.

7. The aerosol-generating system according to claim 5, wherein the air flow through the atomizing nozzle is mixed with the flow of liquid aerosol-forming substrate within the atomizing nozzle and a mixed flow is delivered through a common outlet end.

8. The aerosol-generating system according to claim 5, wherein the air flow through the atomizing nozzle and the flow of liquid aerosol-forming substrate are delivered through separate channels having separate outlet ends.

9. The aerosol-generating system according to claim 5, wherein the heater element is embedded in a heat resistive material.

10. The aerosol-generating system according to claim 5, wherein the atomizing nozzle is configured to produce a specific spray pattern having a geometry and size that corresponds to a shape of the heater element.

11. The aerosol-generating system according to claim 5, further comprising:

a main unit including, a power supply, a control unit, and the atomizing assembly of claim 6; and the liquid storage portion removably coupled to the main unit.

12. A method for generating an aerosol, comprising:

providing an aerosol generating device including an atomizing assembly, the atomizing assembly including, an atomizing nozzle defining an air channel, the air channel configured to establish an air flow through the atomizing nozzle;

a liquid storage portion configured to store a liquid aerosol-forming substrate; and a tubing section having an inlet end and an outlet end, the inlet end of the tubing section being connectable to the liquid storage portion, and the outlet end of the tubing section being in fluid communication with the atomizing nozzle, the tubing section being configured to deliver a flow of the liquid aerosol-forming substrate through the atomizing nozzle, the air flow being mixed with the flow of liquid aerosol-forming substrate delivered through the atomizing nozzle;

delivering a flow of the liquid aerosol-forming substrate through the atomizing nozzle;

mixing the air flow with the flow of the liquid aerosol-forming substrate to form a spray; and delivering the spray to a heating element, the heating element spaced apart from the atomizing nozzle.

13. The method for generating an aerosol according to claim 12, further comprising:

guiding at least a portion of the air flow through the air channel of the atomizing nozzle.

\* \* \* \* \*